United States Patent
Lingnau et al.

(10) Patent No.: US 7,244,438 B2
(45) Date of Patent: Jul. 17, 2007

(54) USES FOR POLYCATIONIC COMPOUNDS

(75) Inventors: Karen Lingnau, Vienna (AT); Frank Mattner, Vienna (AT); Walter Schmidt, Vienna (AT); Michael Buschle, Perchtoldsdorf (AT)

(73) Assignee: Intercell AG, Vienna (AT)

( * ) Notice: Subject to any disclaimer, the term of this patent is extended or adjusted under 35 U.S.C. 154(b) by 0 days.

(21) Appl. No.: 10/250,953

(22) PCT Filed: Jan. 7, 2002

(86) PCT No.: PCT/EP02/00062

§ 371 (c)(1),
(2), (4) Date: Jul. 3, 2003

(87) PCT Pub. No.: WO02/053184

PCT Pub. Date: Jul. 11, 2002

(65) Prior Publication Data

US 2004/0071719 A1    Apr. 15, 2004

(30) Foreign Application Priority Data

Jan. 5, 2001  (EP) .................. PCT/EP01/00087
Apr. 25, 2001  (AT) .................. A 672/2001

(51) Int. Cl.
| A61K 39/00 | (2006.01) |
| A61K 45/00 | (2006.01) |
| A61K 31/00 | (2006.01) |
| A61K 31/70 | (2006.01) |
| C07K 2/00  | (2006.01) |

(52) U.S. Cl. .................. 424/278.1; 424/280.1; 424/282.1; 424/184.1; 514/1; 514/4; 514/44

(58) Field of Classification Search ............ 424/184.1, 424/185.1, 193, 209.1, 278.1, 279.1, 280.1, 424/282.1, 285.1; 514/2, 12, 13, 14, 15, 514/16, 17, 44; 530/300, 350
See application file for complete search history.

(56) References Cited

U.S. PATENT DOCUMENTS

| 5,109,026 | A    | 4/1992 | Hoskinson et al. ......... 514/777 |
| 6,528,058 | B1 * | 3/2003 | Edgar et al. ............. 424/184.1 |
| 6,544,518 | B1 * | 4/2003 | Friede et al. ............ 424/184.1 |
| 6,589,940 | B1 * | 7/2003 | Raz et al. .................... 514/44 |

FOREIGN PATENT DOCUMENTS

| GB | 744988      | 2/1956  |
| GB | 1290141     | 9/1972  |
| JP | 2000256196  | 9/2000  |
| WO | WO 91/04052 | 9/1990  |
| WO | WO 97/10840 | 3/1997  |
| WO | WO 97/30721 | 8/1997  |
| WO | WO 99/38528 | 8/1999  |
| WO | WO 00/00214 | 1/2000  |
| WO | WO 00/41679 | 7/2000  |
| WO | WO 00/62800 | 10/2000 |
| WO | WO 01/24822 | 4/2001  |
| WO | WO 01/34206 | 5/2001  |
| WO | WO 01/93905 | 6/2001  |
| WO | WO 01/93903 | 12/2001 |
| WO | WO 02/13857 | 2/2002  |
| WO | WO 02/32451 | 4/2002  |

OTHER PUBLICATIONS

Mirchamsy et al., Biologicals, vol. 24 No. 4, pp. 343-350 (Dec. 1996).*
Boucher et al. Infection and Immunity, vol. 62 No. 2, pp. 449-456 (Feb. 1994).*
Marshall et al., "Superior Activity of the Type C Class of ISS In Vitro and In Vivo Across Multiple Species," DNA and Cell Biology, vol. 24 No. 2, pp. 63-72 (2005).*
Andreu and Rivas, "Animal Antimicrobial peptides: an overview," Biopoly, 47:415-433, 1998.
Ballas et al., "Induction of nk activity in murine and human cells by cpg motifs in oligodeoxynucleotides and bacterial dna," J. Immunology, 157:1840-1845, 1996.
Bloom and Widdus, "Vaccine visions and their global impact," Nature Med. Vacc. Supp., 4;480484, 1998.
Buschle et al., "Development of defined synthetic vaccines by in vivo charging of antigen presenting cells with antigen," J. Invest. Derma., 114:235, Abstract, 2000.
Buschle et al., "Transloading of tumor antigen-derived peptides into antigen-presenting cells," Proc. Natl. Acad. Sci. USA, 94:3256-3261, 1997.
Buschle et al., "Chemically defined, cell-free cancer vaccines: use of tumor antigen-derived peptides or polyepitope proteins for vaccination," Gene Ther. Mol. Biol., 1:309-321, 1998.
Chace et al., "Bacterial dna-induced nk cell ifn-γ production is dependent on macrophage secretion of IL-12," Clin. Immunol. and Immunopathology, 84:185-193, 1997.
Co-pending U.S. Appl. No. 10/344,709, (SONN:030US) filed Feb. 14, 2003, by Jörg Fritz et al.
Davis et al., "CpG dna is a potent enhancer of specific immunity in mice immunized with recombinant hepatitis b surface antigen," J. Immunology, 160:870-876, 1998.
Deng et al., "Intra-articularly localized bacterial dna containing cpg motifs induces arthritis," Nature Med., 5:702-705, 1999.
Gall et al., "Adjuvant activity of polyelectrolytes," Immunology, 23:569-575, 1972.

(Continued)

Primary Examiner—Bruce R. Campell
Assistant Examiner—Zachariah Lucas
(74) Attorney, Agent, or Firm—Fulbright & Jaworski (57) ABSTRACT

The invention relates to the use of a polycationic compound for the preparation of a medicament with retarded in vivo release.

4 Claims, 5 Drawing Sheets

OTHER PUBLICATIONS

Ganz and Lehrer, "Antibiotic peptides from higher eukaryotes: biology and applications," *Molecular Medicine Today*, 5:292-297, 1999.

Ganz, "Enhanced: defensins and host defense," *Science*, 286:420-421, 1999.

Hancock, "Host defence (cationic) Peptides, what is their future clinical potential?" *Drugs*, 57:469-473, 1999.

Hartmann et al., "CpG dna: a potent signal for growth, activation, and maturation of human dendritic cells," *Proc. Natl. Acad. Sci. USA*, 96:9305-9310, 1999.

Hoffmann et al., "Phylogenetic perspectives in innate immunity," *Science*, 284:1313-1317, 1999.

Immunology, Fifth Edition, Roitt, Beastoff, Nale, eds., 1998.

Klinman et al., "CpG motifs present in bacterial dna rapidly induce lymphocytes to secrete interleukin 6, interleukin 12, and interferon γ," *Proc. Natl. Acad. Sci. USA*, 93:2879-2883, 1996.

Krieg et al., "CpG motifs in bacterial dna trigger direct b-cell activation," *Nature*, 374:546-549, 1995.

Krieg et al., "The role of CpG dinucleotides in dna vaccines," *Trends in Microbiology*, 6:23-27, 1998.

Krieg, "An innate immune defense mechanism based on the recognition of cpg motifs in microbial dna," *J. Lab. Clin. Med.*, 128:128-133, 1996.

Krieg, "CpG dna: a novel immunomodulator," *Trends in Microbiology*, 7:64 1999.

Lethe et al., "Mouse tumor rejection antigens P815A and P815B: two epitopes carred by a single peptide," *Eur. J. Immunol.*, 22:2283-2288, 1992.

Liebert, "CpG: the double-edged sword," *Human Gene Therapy*, 10:2089-2090, 1999.

Liljeqvist and Stahl, "Production of recombinant subunit vaccines: protein immunogens, live delivery systems and nucleic acid vaccines," *J. Biotech.*, 73:1-33, 1999.

Lipford et al., "Bacterial dna as immune cell activator," *Trends in Microbiology*, 6:496-500, 1998.

McCluskie et al., "Novel strategies using dna for the induction of mucosal immunity," *Critical Reviews in Immunology*, 19:303-329, 1999.

Mosmann et al., "Two types of murine helper t cell clone," *J. Immunol.*, 136:2347-2357, 1986.

Nossal, "Living up to the legacy," *Nature Med. Vaccine Suppl.*, 4:475-476, 1998.

Oxenius et al., "CpG-containing oligonucleotides are efficient adjuvants for induction of protective antiviral immune responses with t-cell peptide vaccines," *J. Virology*, 73:4120-4126, 1999.

Pamer et al., "Precise prediction of a dominant class I MHC-restricted epitope of listeria monocytogenes," *Nature*, 353, 852-855, 1991.

Parronchi et al., "Phosphorothioate oligodeoxynucleotides promote the in vitro development of human allergen-specific CD4+ t cells into th1 effectors," *J. Immunology*, 163:5946-5953, 1999.

Pisetsky, Immunostimulatory dna: a clear and present danger? *Nature Medicine*, 3:829-831, 1997.

Pisetsky, The Influence of base sequence on the immunostimulatory properties of dna, *Immunologi Res.*, 19:35-46, 1999.

Rodrigues et al., "The in vivo cytotoxic activity of CD8+ t cell clones correlates with their levels of expression of adhesion molecules," *J. Exp. Med.*, 175:895-905, 1992.

Rotzschke et al., "Exact prediction of a natural t cell epitope," *Eur. J. Immunol.*, 21:2891-2984, 1991.

Schmidt et al., "Cell-free tumor antigen peptide-based cancer vaccines," *Proc. Natl. Acad. Sci. USA*, 94:3262-3267, 1997.

Schwartz et al., "CpG motifs in bacterial dna cause inflammation in the lower respiratory tract," *J. Clin. Invest.*, 100:68-73, 1997.

Shimonkevits et al., "Antigen recognition by h-2-restricted t cells," *J. Immunol.*, 133: 2067-2075, 1984.

Simmaco et al., "Antimicrobial peptides from amphibian skin: what do they tell us?" *Biopoly*, 47:435-450, 1998.

Sparbier and Walden, "T cell receptor specificity and mimotopes," *Current Opin. Immun.*, 11:214-218, 1999.

Sparwasser et al., "Bacterial dna and immunostimulatory CpG oligonucleotides trigger maturation and activation of murine dendritic cells," *Eur. J. Immunol.*, 28:2045-2054, 1998.

Sparwasser et al., "Bacterial dna causes septic shock," *Nature*, 386:336-337, 1997.

Sparwasser et al., "Macrophages sense pathogens via dna motifs: induction of tumor necrosis factor-α-mediated shock," *Eur. J. Immunol.*, 27:1671-1679, 1997.

Weiner et al., "Immunostimulatory oligodeoxynucleotides containing the cpg motif are effective as immune adjuvants in tumor antigen immunization," *Proc. Natl. Acad. Sci. USA*, 94:10833-10837, 1997.

Yew et al., "Contribution of Plasmid dna to inflammation in the lung after administration of cationic lipid:pdan complexes," *Human GeneTherapy*, 10:223-234, 1999.

* cited by examiner

USES FOR POLYCATIONIC COMPOUNDS

This application is a U.S. national phase application under 35 U.S.C. § 371 of PCT Application No. PCT/EP02/00062 filed 7 Jan. 2002, which claims priority to Austrian Application No. A 672/2001 filed 25 Apr. 2001 and PCT Application No. PCT/EP01/00087 filed 5 Jan. 2001.

The invention relates to new uses for polycationic compounds.

Pharmaceutically used polycationic compounds, for example the polycationic amino acid polymers poly-L-arginine and poly-L-lysine, have been shown to allow very efficient charging of antigen presenting cells (APCs) with antigens in vitro and in vivo. This is thought to be the key event for triggering immune cascades, eventually leading to the induction of antigen specific immune effector cells that are able to destroy or neutralise targets. It has been shown previously that a number of polycationic compounds excert effects on immune cells (Buschle et al., Gene Ther. Mol. Biol. 1 (1998), 309–321; Buschle et al., Proc. Natl. Acad. Sci. USA, 94 (1997), 3256–3261).

Co-injection of a mixture of poly-L-arginine and poly-L-lysine together with an appropriate antigen as a vaccine protects animals from tumor growth in several animal models. A vaccine consisting of polycationic compounds and antigens is accepted in the art as being a very effective form of treatment (WO 97/30721).

Many pharmaceutical substances administered to an individual are often quickly distributed throughout the body. The rapid systemic distribution of the drug usually causes strong and harmful side effects. The medical effect would be better if the medicament would stay in higher amounts at the site of administration and be gradually and continuously released to the whole body in small amounts.

It is an object of the present invention to provide means for keeping a medicament which is desired to act locally at the site of administration (depot effect). It is a further object of the invention to prevent or ameliorate side effects of drugs which are due to a too fast distribution of this drug throughout the body.

These objects are solved by the use of a polycationic compound for the preparation of a medicament with retarded in vivo release. It has surprisingly been found out in the course of the present invention that polycationic compounds, if applied together with other pharmaceutically active compounds, which are quickly distributed in the individual, when administered without polycationic compounds, exhibit an effect of a retarded release of the active compound from the site of administration. The polycationic compound seems to keep the active pharmaceutical compound in a depot which allows a retarded in vivo release of the medicament which is often desired for an effective treatment with the pharmaceutically active principle.

An important field, where such a retarded in vivo release is advantageous is vaccination. If an antigen is presented for an extended period of time to the immune system of an individual to be vaccinated, the immune system has an enhanced possibility to create an efficient immune response against such an antigen. If, on the other hand, such an antigen is quickly distributed throughout the body, the antigen is quickly degraded and diluted so that an efficient immune response may not be achieved for many promising antigens. According to the present invention polycationic compounds therefore are used for providing a depot of e.g. such an antigen, which allows a long lasting continuous and effective presentation of this antigen to the immune system in order to create a protective immunity. Furthermore, when the antigens are applied in combination with immunostimulatory compounds (e.g. CpG-ODN), the slow release of these immunostimulatory compounds from the depot should result in a continuous stimulation of the immune system.

The present invention is especially beneficial if the combined medicament is administered, e.g. subcutaneously, intravenously, intranasally, intramusculary, intradermally or transdermally. However, other application forms, such as parenteral or topical application, are also suitable for the present invention. However, the depot effect seems to be mostly significant if the composition is injected or implanted.

The present invention is preferably used in connection with all medicaments for which a retarded in vivo release is desired, e.g. antigens, allergens, drugs, which include cytokines, chemokines, immunostimulatory nucleic acids, cytotoxic drugs or anti-angiogenic drugs or compounds needed for wound healing.

The antigen to be used within the course of the present invention is not critical, it may preferably be selected from the group consisting of an antigen from a viral, bacterial or a parasitic pathogen, an antigen from an eucaryotic pathogen, a tumor antigen, an autoimmune antigen or mixtures thereof. Especially preferred are negatively charged antigens or hydrophobic antigens. Further examples of antigens are whole-killed organisms, such as inactivated viruses or bacteria, fungi, protozoa or even cancer cells. Antigens may also consist of subfractions of these organisms/tissues, of proteins, or, in their most simple form, of peptides. Antigens can also be recognised by the immune system in form of glycosylated proteins or peptides and may also be or contain polysaccharides or lipids. Short peptides can be used, since e.g. cytotoxic T cells (CTL) recognise antigens in form of short usually 8–11 amino acids long peptides in conjunction with major histocompatibility complex (MHC). B cells recognise longer peptides starting at around 15 amino acids. By contrast to T cell epitopes, the three dimensional structure of B cell antigens may also be important for recognition by antibodies.

Preferred pathogens are selected from human immune deficiency virus (HIV), hepatitis A and B viruses, hepatitis C virus (HCV), Rous sarcoma virus (RSV), Epstein Barr virus (EBV), Influenza virus, Rotavirus, *Staphylococcus aureus, Chlamydia pneumoniae, Chlamydia trachomatis, Mycobacterium tuberculosis, Streptococcus pneumoniae, Bacillus anthracis, Vibrio cholerae, Plasmodium* sp. (*Pl. falciparum, Pl. vivax*, etc.), *Aspergillus* sp. or *Candida albicans*. Antigens may also be molecules expressed by cancer cells (tumor antigens). Antigens may also be derived antigens. The derivation process may include the purification of a specific protein from the pathogen/cancer cells, the inactivation of the pathogen as well as the proteolytic or chemical derivatisation or stabilisation of such a protein. In the same way also tumor antigens (cancer vaccines) or autoimmune antigens may be used together with a polycationic compound according to the present invention.

The polycationic compound(s) to be used according to the present invention may be any polycationic compound, which shows e.g. the characteristic effect according to the WO 97/30721, or others like cationic liposomes, polyethylene-amine, chitosan or polycations for DNA transfer. Preferred polycationic compounds are selected from basic polypeptides, organic polycations, basic polyaminoacids or mixtures thereof. These polyaminoacids should have a chain length of at least 4 amino acid residues (see: Tuftsin as described in Goldman et al (1983)). Especially preferred are substances containing peptidic bounds, like polylysine, polyarginine and polypeptides containing more than 20%, especially more than 50% of basic amino acid residues in a range of more than 8, especially more than 20, amino acid residues or mixtures thereof. Other preferred polycations and their pharmaceutical compositons are described in WO 97/30721 (e.g. polyethyleneimine) and WO 99/38528. Preferably these polypeptides contain between 5 and 500 amino acid residues, especially between 10 and 200 residues.

These polycationic compounds may be produced chemically or recombinantly or may be derived from natural sources.

Cationic (poly)peptides may also be polycationic antibacterial microbial peptides with properties as reviewed in (Ganz and Lehrer, 1999; Hancock, 1999). These (poly) peptides may be of prokaryotic or animal or plant origin or may be produced chemically or recombinantly (Andreu and Rivas, 1998; Ganz and Lehrer, 1999; Simmaco et al., 1998). Peptides may also belong to the class of defensins (Ganz, 1999; Ganz and Lehrer, 1999). Sequences of such peptides can, for example, be found in the Antimicrobial Sequences Database under the following internet address:
http://www.bbcm.univ.trieste.it/~tossi/pag1.html Such host defense peptides or defensines are also a preferred form of the polycationic polymer according to the present invention. Generally, a compound allowing for activation (or down-regulation) of the adaptive immune system, preferably mediated by APCs (including dendritic cells) is used as polycationic polymer.

Especially preferred for use as polycationic substance in the present invention are cathelicidin derived anti-microbial peptides or derivatives thereof (A 1416/2000, incorporated herein by reference), especially anti-microbial peptides derived from mammal cathelicidin, preferably from human, bovine or mouse.

Polycationic compounds derived from natural sources include HIV-REV or HIV-TAT (derived cationic peptides, antennapedia peptides, chitosan or other derivatives of chitin) or other peptides derived from these peptides or proteins by biochemical or recombinant production. Other preferred polycationic compounds are cathelin or related or derived substances from cathelin. For example, mouse cathelin is a peptide which has the amino acid sequence NH$_2$-RLAGLLRKGGEKIGEKLKKIGOKIKN-FFQKLVPQPE-COOH. Related or derived cathelin substances contain the whole or parts of the cathelin sequence with at least 15–20 amino acid residues. Derivations may include the substitution or modification of the natural amino acids by amino acids which are not among the 20 standard amino acids. Moreover, further cationic residues may be introduced into such cathelin molecules. These cathelin molecules are preferred to be combined with the antigen and the immunogenic ODNs according to the present invention. However, these cathelin molecules surprisingly have turned out to be also effective as an adjuvant-for an antigen without the addition of further adjuvants. It is therefore possible to use such cathelin molecules as efficient adjuvants in vaccine formulations with or without further immunostimulating substances.

Another preferred polycationic substance to be used according to the present invention is a synthetic peptide containing at least 2 KLK-motifs separated by a linker of 3 to 7 hydrophobic amino acids (A 1789/2000, incorporated herein by reference).

As mentioned above polycationic compounds may according to the present invention be preferably used together with a drug for which side effects due to a quick spread throughout the body of an individual are known. In general, the polycationic compound and the drug supposed to be released slowly are administered together at the same time and at the same site. In the combined medicament according to the present invention, such drugs may be e.g. simply mixed with the polycationic compounds or provided as a covalently combined medicament.

Preferred compounds with inflammatory potential to be used within the course of the present invention are immunogenic nucleic acid molecules. It is known that the immune system of mammals (and probably most if not all vertebrates) recognises DNA of lower organisms, including bacteria probably due to structural and sequence usage differences between pathogen and host DNA. In particular, short stretches of DNA derived from non-vertebrates or short form oligodeoxynucleotides (ODNS) containing non-methylated cytosine-guanine dinucleotides (CpG) in a certain base context, are targeted. CpG motifs are found at the expected frequency in bacterial DNA but are much less frequent in vertebrate DNA. In addition, non-vertebrate (i.e. bacterial) CpG motifs are not methylated, whereas vertebrate CpG sequences are. Such ODNs containing CpG motifs (CpG-ODNs) can directly activate monocytes and B cells. In consequence, the activation of monocytes and NK cells by CpG-ODNs promotes the induction of a Th1-type response and the development of cytotoxic T cells. In addition; such immunogenic ODNs are used as vaccine adjuvants to enhance the antibody response to specific antigens (e.g. EP 0 468 520 A2, WO 96/02555, WO 98/16247, etc.).

When CpG-ODNs are applied in combination with an antigen to an animal, the CpG-ODN molecules are quickly distributed throughout the body without providing an effective minimum concentration at the site of administration where the desired effect should be initiated. It could be shown by the present animal model that the polycationic compounds inhibit the immediate spread of these molecules and induce the formation of a depot of CpG-ODNs at the injection site which resulted in a strongly prolonged CpG-ODN induced antigen specific immune response in vivo. This CpG-ODN model therefore was excellent for showing the depot effect of polycationic compounds. If CpG-ODNs are applied in combination with an antigen via injection, the CpG-ODN molecules are quickly distributed throughout the body without providing an effective minimum concentration at the site of administration where the desired effect should be initiated. It could be shown by the present animal model that the polycationic compounds inhibit the immediate spread of these molecules and induce the formation of a depot antigen and CpG-ODNs at the injection site, which resulted in a strongly prolonged CpG-ODN induced antigen-specific immune response in vivo.

Therefore, a preferred embodiment of the present invention is characterised in that the medicament is to be applied together with the polycationic compound further comprises immunogenic oligodesoxy nucleic acid molecules (ODNs), especially ODNs containing CpG motifs (CpG-ODNs), inosine containing ODNs (I-ODNs) or mixtures or combinations thereof. I-ODNs are described for example in the Austrian patent application A 1973/2000 (incorporated herein by reference). Mixtures of I-ODNs with CpG-ODNs may also be provided as well as combinations of these two principles, e.g. an I-ODN containing CpG motifs.

The induction of a depot effect according to the present invention is of course most desired for pharmaceutically active substances which are supposed to act locally at the given administration site. Therefore, the invention is significantly advantageous for substances, which should act locally but are easily transported and diffused away from this site by diffusion of transportation processes in the body. Such substances may include antigens, allergens, cytokines, chemokines, immunostimulatory nucleic acids, cytotoxic drugs or anti-angiogenic drugs or compound needed for wound healing.

A preferred embodiment of the present invention relates to the use of the polycationic substances in combination with substances which otherwise rapidly diffuse from the administration site, i.e. have a rather short pharmacological half life, especially with respect to the site of administration. Therefore, preferred rapidly diffusing substances with a pharmacological half life (drop of the concentration of the substance by half), especially at the site of administration, of below 10 minutes, more preferred below 5 minutes, especially below 1 minute.

Preferably, such substances to be applied together with polycationic compounds in order to achieve a depot effect show a certain affinity to the polycationic compound, i.e. hydrophobic interaction, hydrogen bridges, electrostatic interactions, polar or ionic interactions. Of course, the depot effect may also be achieved by covalent binding of the components in the combined pharmaceutical preparation; although non-covalent interactions of drug and polycationic compounds are preferred.

It is known (PCT/EP 01/00087) that the co-application of polycationic compounds and CpG-ODNs with an antigen strongly and synergistically enhances the induction of an antigen specific immune response when compared to the injection without poly-cationic compounds. That is reflected by a high number of IFN-γ-producing cells isolated from draining lymph nodes (ELISPOT assay). As stated above within the course of the present invention, it could be shown that this strong local immune response (day 4/draining lymph node cells) induced after one single injection of an antigen with a mixture of polycationic compounds (as an example polyarginine pR 60 is used) and CpG-ODNs converts to a systemic immune response which is very long lasting. According to the present invention, the complex formation ability of substances such as CpG-ODNs with polycationic compounds is used for preventing a systemic distribution and the subsequent fast resorption of such substances, thereby providing a strong prolongation of the properties of such substances, e.g. a prolongation of the immunostimulatory properties of CpG-ODNs. In addition, preventing the systemic distribution avoids the induction of potential harmful systemic side effects of immunostmulatory agents.

This model using CpG-ODNs and polycationic peptides is further described and analysed in the example section. Moreover, to provide an analysable pharmaceutical target, an Ovalbumin-derived peptide ($OVA_{257-264}$) is used as a model compound (a model antigen).

The present invention also relates to treating a patient with a drug, supposed to be retardedly released in vivo comprising administering that drug together with an effective amount of a polycationic compound inducing a depot effect of that drug.

The amounts of polycationic compound to be administered is highly depending on the necessities of the individual composition and optionally on the drug to be administered together with the polycationic polymer. In case of poly-L-arginine and poly-L-lysine preferred amounts of polycation are 0.001–1000 μg/administration unit, more preferred 0,1–10 mg/dose, especially around or beyond 0,1 mg/20 g body weight (of mice) or the equivalent dose for humans.

The invention will be described in more detail by way of the following examples and the drawing figures, yet it is not restricted to these particular embodiments.

EXAMPLES

In the present examples it is shown that the strong local immune response (day 4/draining lymph node cells) induced after one single injection of antigen with a mixture of pR60 and CpG-ODN converts to a systemic immune response which is, most importantly, very long lasting (Example 1). Even 372 days after injection (the latest time point analysed), around 500 antigen-specific, IFN-g producing T cells per million peripheral blood lymphocytes can be detected. One possible explanation for this effect might be that a complex-formation of CpG-ODN with poly-L-arginine prevents the systemic distribution of CpG-ODN and the subsequent fast resorption of CpG-ODN. Hence, this results in a strong prolongation of the immunostimulatory properties of CpG-ODNs.

Figure 2A:
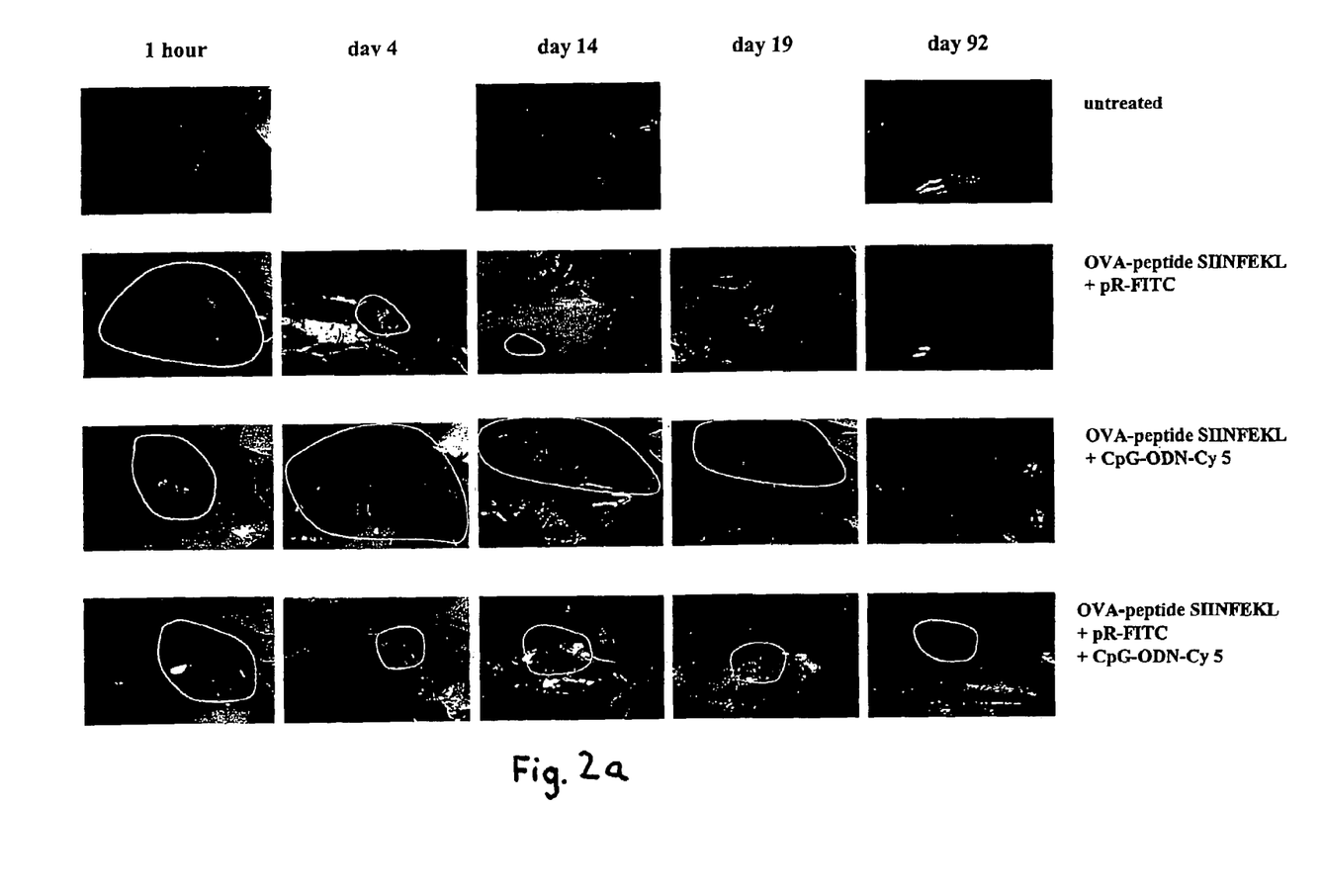
FIG. 2a shows that poly-L-arginine induces the formation of a depot at the injection site. This figure shows photos from the injection sites at the indicated time points after vaccination. White lines surround the area where the fluorescence labelled compounds of the vaccine can be detected.
Figure 2B:
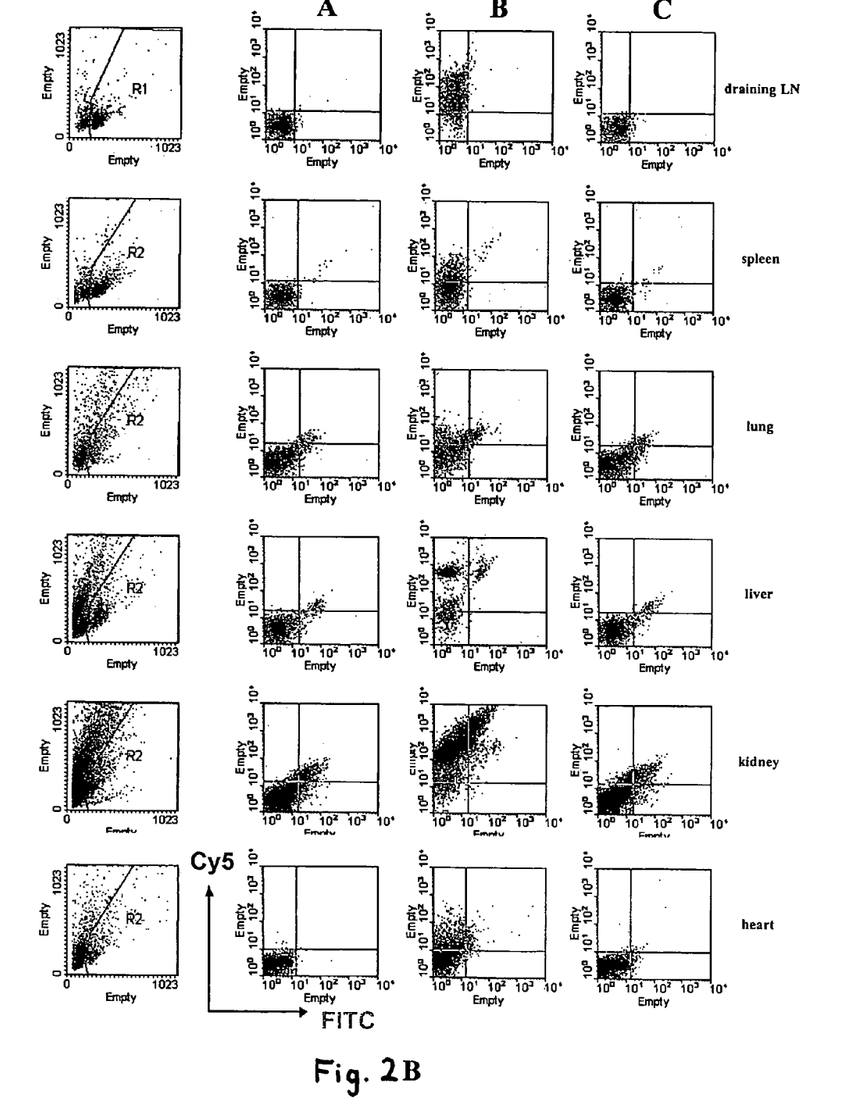
FIG. 2b shows that the co-application of poly-L-arginine inhibits the spreading of CpG-ODN-Cy5 throughout the body. This figure shows FACS analyses of lymphoid and non-lymphoid tissues at day 1 after injection of CpG-ODN-Cy5 (B) or CpG-ODN-Cy5 and pR 60-FITC (C). Untreated mice were used as a control (A)

In order to investigate this assumption, fluorescence-labeled compounds were injected together subcutaneously into the flank of mice. At different time points after this treatment, injection sites were inspected for the presence of labeled compounds. In example 2a and 2b, $OVA_{257-264}$-peptide (unlabeled), poly-L-arginine-FITC (yellow) and CpG-ODN-Cy5 (blue) were used for injections. After injection of $OVA_{257-264}$-peptide with poly-L-arginine-FITC the formation of a depot could be detected at the injection site. The injection of $OVA_{257-264}$-peptide with CpG-ODN-Cy5 resulted in the distribution of CpG-ODN-Cy5 all over the skin (example 2a). As simultaneously determined by FACS analyses (example 2b), CpG-ODN-Cy5 is also detectable in secondary lymphoid organs (draining lymph node, spleen) and non-lymphoid tissues (lung, liver, kidney, heart). In contrast, when $OVA_{257-264}$-peptide and CpG-ODN-Cy5 were injected together with poly-L-arginine-FITC, the CpG-ODN-Cy5 was restricted to the depot formed by poly-L-arginine (example 2a). FACS analyses from these mice (example 2b) revealed that CpG-ODN-Cy5 is not detectable in the periphery, due to the fact that CpG-ODN-Cy5 is trapped by poly-L-arginine in the depot at the injection site.

Figure 3:
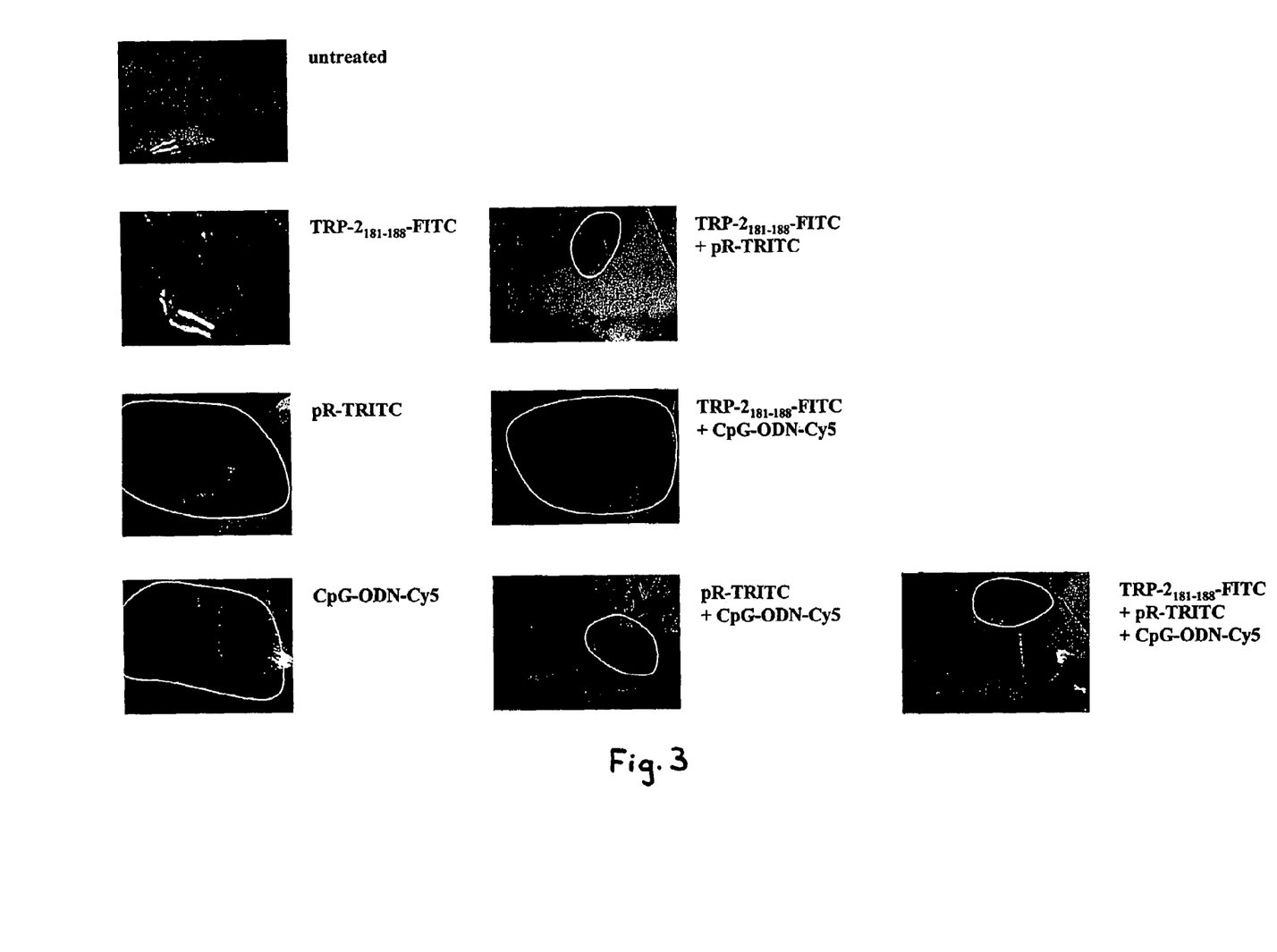
FIG. 3 shows that poly-L-arginine induces the formation of a depot at the injection site when co-injected at least with one more molecule. This figure shows photos from the injection sites at day 4 after vaccination.

Both, poly-L-arginine-FITC and CpG-ODN-Cy5 can be detected within this depot at least up to day 92 after injection (the latest time point analysed). This observation implies that the combination of peptide and poly-L-arginine with CpG-ODN led to a far long lasting existence of the depot compared to the combination of peptide and poly-L-arginine. In example 3, TRP-2$_{181-188}$-peptide-FITC (yellow), poly-L-arginine-TRITC (red-violet), CpG-ODN-Cy5 (blue) were used for injections. When TRP-2$_{181-188}$-peptide-FITC was injected either alone or in combination with CpG-ODN-Cy5, the peptide was not detectable at the injection site at day 4. The injection of poly-L-arginine-TRITC alone resulted in its distribution all over the skin. The injection of CpG-ODN-Cy5 either alone or in combination with TRP-2-peptide-FITC resulted in the distribution of CpG-ODN-Cy5 all over the skin. This experiment also indicates that poly-L-arginine only-induced the formation of a depot when it was injected with at least one more molecule (peptide and/or CpG-ODN).

Thus, these findings imply that poly-L-arginine induces a depot at the injection site within other compounds (antigen and/or immunostimulatory CpG-ODN) are kept. In the case of co-injection of OVA$_{257-264}$-peptide, poly-L-arginine and CpG-ODN, the slow release of both peptide and CpG-ODN from this depot is most likely responsible for the persistent activation of accessory cells and subsequently the persistent stimulation of T cells. In consequence, this leads to the observed long lasting existence of high numbers of antigen-specific T cells in the periphery after one single injection.

Beside their potent immunostimulatory effects, CpG-ODNs are described to have potentially harmful side effects in that they induce the systemic release of high amounts of pro-inflammatory cytokines such as TNF-α and IL-6, which could induce a shock syndrome (Sparwasser 1997, Lipford 1997). As described in example 2a, 2b and 3, CpG-ODNs are not systemically present when injected in combination with poly-L-arginine. Therefore, it was investigated whether the co-administration of poly-L-arginine affects the CpG-ODN-induced systemic production of TNF-α and IL-6. Serum levels of both cytokines were determined by ELISA one hour after injection. Example 4 demonstrates that neither the injection of OVA$_{257-264}$-peptide alone nor in combination with poly-L-arginine led to the induction of significant amounts of TNF-α and IL-6 in the serum, whereas the injection of OVA$_{257-264}$-peptide in combination with CpG-ODN induces high concentrations of both cytokines. However, upon co-administration of OVA$_{257-264}$-peptide with poly-L-arginine and CpG-ODN, this systemic production of TNF-α and IL-6 was totally abolished. Thus, these data in combination with the findings demonstrated in Example 2 and 3 indicate that the localization of CpG-ODN via the depot formation mediated by poly-L-arginine prevents the systemic distribution of CpG-ODN and subsequently the systemic release of pro-inflammatory cytokines.

In parallel, in vitro studies were performed to clarify whether the complexation of CpG-ODN by poly-L-arginine can also directly influence the stimulation of mouse bone marrow-derived CD11c$^+$ dendritic cells by CpG-ODN concerning the production of TNF-α and IL-6. For this purpose, CD11c$^+$ dendritic cells were incubated either with poly-L-arginine, CpG-ODN or the combination of poly-L-arginine and CpG-ODN (example 5). The levels of TNF-a and IL-6 were determined in the supernatants derived from these cultures. After incubation with poly-L-arginine neither TNF-α nor IL-6 were detectable, whereas after incubation with CpG-ODN significant amounts of both cytokines are produced. Impressively, the presence of poly-L-arginine inhibited the CpG-ODN-induced production of TNF-α and IL-6 by these cells.

Thus, these results indicate that the complexation of CpG-ODN by poly-L-arginine not only inhibits the systemic but also the local release of pro-inflammatory cytokines. In consequence, these beneficial effects of poly-L-arginine prevent probably uncontrolled and excessive systemic and local immune responses induced by CpG-ODNs.

Further in vitro-experiments revealed that poly-L-arginine also inhibits the polyinosinic-polycytidylic acid-induced production of pro-inflammatory cytokines by human dendritic cells.

Thus, these observations imply a general anti-inflammatory effect of poly-L-arginine. The risks of the application of immunogenic but potential harmful substances can be probably minimised by the co-application of poly-L-arginine. The rapid systemic distribution of such substances can be prevented by the property of poly-L-arginine to form a depot in which all compounds are trapped. Furthermore, the complexation of these substances by poly-L-arginine can e.g. inhibit the release of toxic amounts of pro-inflammatory cytokines.

Example 1

The Combined Application of Ovalbumin-Peptide/poly-L-arginine (pR 60)/CpG-ODN Leads to the Induction of Strong Antigen-Specific Immune Responses which are Systemic and very Long Lasting.

| Mice | C57Bl/6 (Harlan/Olac) |
|---|---|
| Peptide | OVA$_{257-264}$-Peptide (SIINFEKL), a MHC class I (H-2Kb)-restricted epitope of chicken Ovalbumin (Rotzschke, O. et al., Eur. J. Immunol. 1991 21 (11): 2891–4), synthesised by standard solid phase F-moc synthesis, HPLC purified and analysed by mass spectroscopy for purity. Dose: 300 µg/mouse |
| Poly-L-Arginine 60 (pR60) | Poly-L-Arginine with an average degree of polymerisation of 60 arginine residues; SIGMA chemicals Dose: 100 µg/mouse |
| CpG-ODN 1668 | phosphothioate-modified oligodinucleotides containing a CpG- motif: tcc atg acg ttc ctg atg ct, synthesised by NAPS Göttingen GmbH. Dose: 5 nmol/mouse |

Experimental Groups (5 Mice per Group)
1. OVA$_{257-264}$-Peptide+CpG-ODN+pR 60
2. OVA$_{257-264}$-Peptide+CpG-ODN
3. OVA$_{257-264}$-Peptide+pR 60

Figure 1:
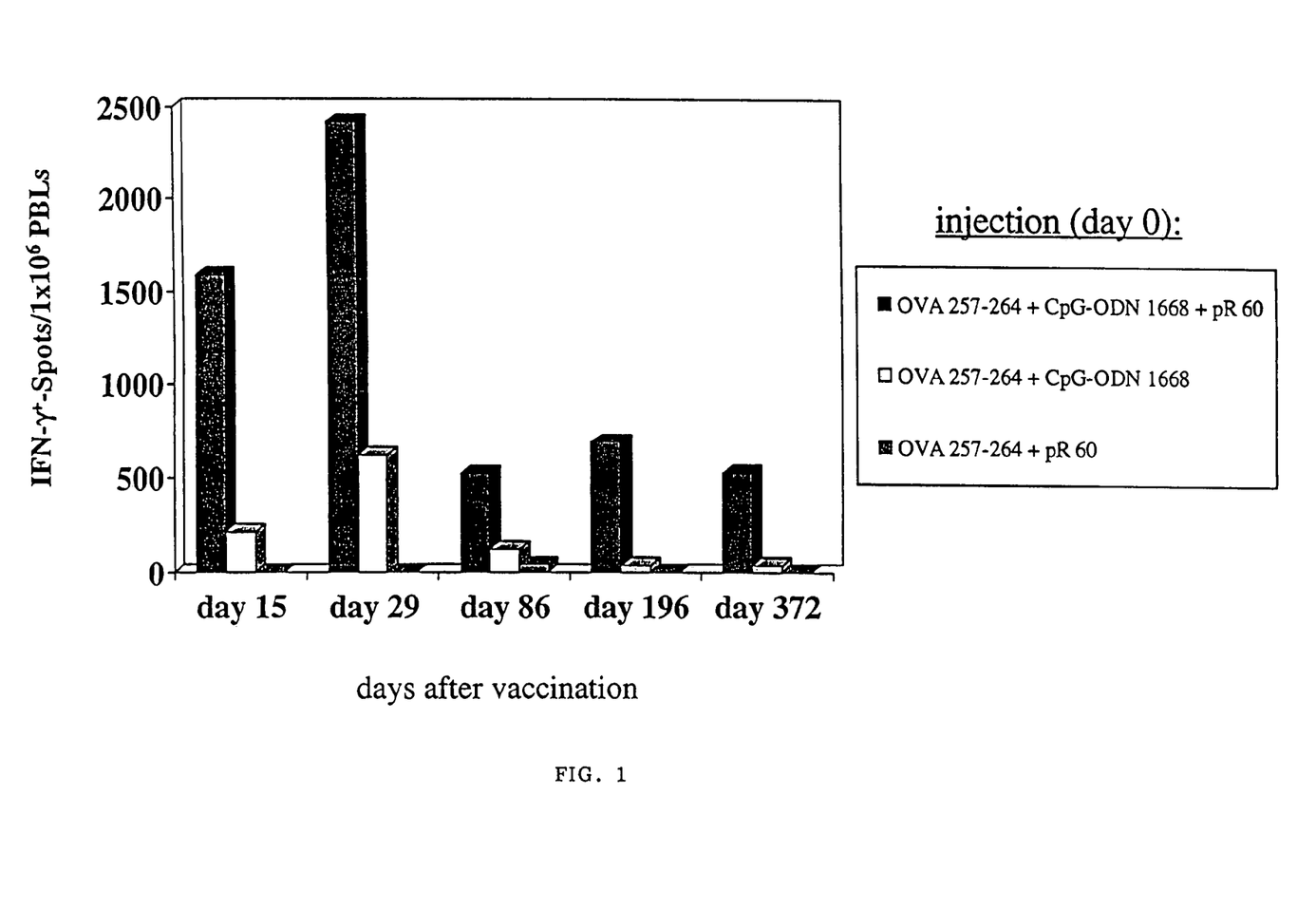
FIG. 1 shows that the combined application of poly-L-arginine, CpG-ODN and antigen induces strong antigen-specific immune responses which are systemic and very long lasting. The figure shows peripheral blood lymphocytes stimulated ex vivo with $OVA_{257-264}$ -peptide.

On day 0, mice were injected into each hind footpad with a total volume of 100 µl (50 µl per footpad) containing the above mentioned compounds. Blood was taken via the tail vein at the indicated time points and peripheral blood lymphocytes (PBLs) were isolated using a Ficoll gradient. PBLs were stimulated ex vivo with the antigen used for vaccination, with medium (background) and Concanavalin A (positive control). IFN-γ-ELISPOTs were carried out as described (Miyahira et al., 1995). This method is a widely used procedure allowing the quantification of antigen-specific T cells. Spots representing single IFN-γ producing T cells were counted and the number of background spots was substracted from all samples. There were many spots detected after the stimulation with Con A (data not shown) indicating a good condition of the used lymphocytes. For each experimental group of mice the number of spots/1×10⁶ PBLs are illustrated in FIG. 1.

Example 2a

Poly-L-arginine Induces the Formation of a Depot at the Injection Site

| | |
|---|---|
| Mice | C57Bl/6 (Harlan/Olac) |
| Peptide | OVA$_{257-264}$-Peptide (SIINFEKL), a MHC class I (H-2Kb)-restricted epitope of chicken Ovalbumin (Rotzschke, O. et al., Eur. J. Immunol. 1991 21(11): 2891–4), synthesised by standard solid phase F-moc synthesis, HPLC purified and analysed by mass spectroscopy for purity.<br>Dose: 300 µg/mouse |
| Poly-L-Arginine 60-FITC (pR60-FITC) | Poly-L-Arginine with an average degree of polymerisation of 60 arginine residues; SIGMA chemicals<br>For fluorescein (FITC) labeling of poly-L-arginine, the poly-L-arginine was dissolved in 50 mM HEPES pH 7.9 (10 mg/500 µl). A 5-fold molar excess of FITC (Molecular Probes, Eugene, OR) in an equal volume of DMSO was added to the poly-L-arginine solution. The solution was kept at room temperature in the dark for 2.5 hours. Unreacted dye was separated by running the mixture over a PD10 column (Pharmacia, Uppsala, Sweden), using 50 mM Hepes, pH 7.9, as eluent. The solution was then dialysed against 2 × 5 liter aqua dest., pH 7.4 (0.1 M HCL), over night. After lyophilisation poly-L-arginine FITC was dissolved in aqua bidest. with a concentration of 10 mg/ml.<br>Dose: 100 µg/mouse |
| CpG-ODN 1668-Cy5 | phosphothioate-modified, Cy5-labeled oligodinucleotides containing a CpG motif: tcc at<u>g acg t</u>tc ctg atg ct, synthesised by NAPS Göttingen GmbH.<br>Dose: 5 nmol/mouse |

Experimental Groups (1 Mouse/Group 1/Indicated time Point, 3 Mice/Group 2–4/Time Point)
1. untreated
2. OVA$_{257-264}$-Peptide+pR 60-FITC
3. OVA$_{257-264}$-Peptide+CpG-ODN1668-cy5
4. OVA$_{257-264}$-Peptide+pR 60-FITC+CpG-ODN 1668-Cy5

On day 0 mice were injected subcutaneously into the right flank with a total volume of 100 µl containing the above mentioned compounds. Animals were sacrificed at the indicated time points after injection and photos were taken from the injection sites (FIG. 2a).

Example 2b

Co-Application of Poly-L-arginine Inhibits the Distribution of CpG-ODN-Cy5 throughout the Body

| | |
|---|---|
| Mice | C57Bl/6 (Harlan/Olac) |
| Poly-L-Arginine 60-FITC (pR60-FITC) | Poly-L-Arginine with an average degree of polymerisation of 60 arginine residues; SIGMA chemicals<br>For fluorescein (FITC) labeling of poly-L-arginine, the poly-L-arginine was dissolved in 50 mM HEPES pH 7.9 (10 mg/500 µl). A 5-fold molar excess of FITC (Molecular Probes, Eugene, OR) in an equal volume of DMSO was added to the poly-L-arginine solution. The solution was kept at room temperature in the dark for 2.5 hours. Unreacted dye was separated by running the mixture over a PD10 column (Pharmacia, Uppsala, Sweden) using 50 mM Hepes pH 7.9 as eluent. The solution was then dialysed against 2 × 5 liter aqua dest., pH 7.4 (0.1 M HCL), over night. After lyophilisation poly-L-argine-FITC was dissolved in aqua bidest. with a concentration of 10 mg/ml.<br>Dose: 100 µg/mouse |
| CpG-ODN 1668-Cy5 | phophothioate-modified, Cy5-labeled oligodinucleotides containing a CpG motif: tcc atg <u>acg</u> ttc ctg atg ct, synthesised by NAPS Göttingen GmbH.<br>Dose: 5 nmol/mouse |

Experimental Groups (1 Mouse/Group 1/Indicated Time Point, 3 Mice/Group 2–4/Time Point)
1. untreated
2. CpG-ODN1668-Cy5
3. pR 60-FITC+CpG-ODN 1668-Cy5

Mice were injected subcutaneously into the right flank with a total volume of 100 µl containing the above mentioned compounds. One day after injection, mice were sacrificed and FACS-analyses were performed from secondary lymphoid organs (draining lymph node, spleen) as well as non-lymphoid tissues (lung, liver, kidney, heart) (FIG. 2b).

Example 3

Poly-L-arginine Induces the Formation of a Depot at the Injection Site when Co-Injected at Least with One More Molecule

| | |
|---|---|
| Mice | C57Bl/6 (Harlan/Olac) |
| Peptide | TRP-2-Peptide (VYDFFVWL), a MHC class I (H-2Kb)-restricted epitope of mouse tyrosinase related protein-2 (Bloom, M. B. et al., J Exp Med 1997 185, 453–459), synthesised by standard solid phase F-moc synthesis, HPLC purified and analysed by mass spectroscopy for purity. For fluorescein (FITC) labeling, the TRP-2$_{181-188}$-peptide was dissolved in 1 M sodium borate, pH 7.9. An 8-fold molar excess of FITC (Molecular Probes, Eugene, OR) in an equal volume of DMF was added to the peptide solution. The solution was kept at room temperature for four hours. Unreacted dye was seoarated ba running the mixture over a G25 gel filtration column (Pharmacia, Uppsala, Sweden) using 0.1% TFA in water as eluent. Two moles of FITC were incorporated per mol of peptide (N-terminus, side chain of lysine)<br>Dose: 100 µg/mouse |
| Poly-L-Arginine 60-TRITC (pR60-TRITC) | Poly-L-Arginine with an average degree of polymerisation of 60 arginine residues; SIGMA chemicals. For TRITC-labeling of poly-L-arginine, the poly-L-arginine was dissolved in 50 mM HEPES pH 7.9 (10 mg/500 µl). A 5-fold molar excess of FITC (Molecular Probes, Eugene, OR) in an equal volume of DMSO was added to the poly-L-arginine solution. The solution was kept at room temperature in the dark for 2.5 hours. Unreacted dye was separated by running the mixture over a PD10 column (Pharmacia, Uppsala, Sweden), using 50 mM Hepes, pH 7.9, as eluent. The solution was then dialysed against 2 × 5 liter aqua dest., pH 7.4 (0.1 M HCL), over night. After lyophilisation poly-L-argine-TRITC was dissolved in aqua bidest. with a concentration of 10 mg/ml.<br>Dose: 100 µg/mouse |

-continued

| | |
|---|---|
| CpG-ODN 1668-Cy5 | phosphothioate-modified, Cy5-labeled oligodinucleotides containing a CpG motif: tcc atg acg ttc ctg atg ct, synthesised by NAPS Göttingen GmbH.<br>Dose: 5 nmol/mouse |

Experimental Groups (1 Mouse/Group 1/Indicated Time Point, 3 Mice/Group 2–4/time Point)
1. untreated
2. TRP-2$_{181-188}$-FITC
3. pR60-TRITC
4. CpG-ODN1668-Cy5
5. TRP-2-FITC+pR60-TRITC
6. TRP-2$_{181-188}$-FITC+CpG-ODN-Cy5
7. pR60-TRITC+CpG-ODN 1668-Cy5
8. TRP-2 $_{181-188}$-FITC+pR 60-TRITC+CpG-ODN 1668-Cy5

On day 0 mice were injected subcutaneously into the right flank with a total volume of 100 μl containing the above mentioned compounds. Animals were sacrificed at day 4 after injection and photos were taken from the injection sites (FIG. 3).

Example 4

The Co-Injection of Poly-L-arginine Prevents the CpG-ODN-Induced Systemic Production of TNF-α and IL-6 In Vivo

| | |
|---|---|
| Mice | C57Bl/6 (Harlan/Olac) |
| Peptide | OVA$_{257-264}$ (SIINFEKL), an MHC class I (H-2Kb)-restricted epitope of chicken ovalbumin (Rotzschke et al., 1991), was synthesised using standard solid phase F-moc synthesis, HPLC-purified and analysed by mass spectroscopy for purity<br>Dose: 300 μg/mouse |
| Poly-L-arginine 60 (pR60) | Poly-L-arginine with an average degree of polymerisation of 60 arginine residues; SIGMA Chemicals<br>Dose: 100 μg/mouse |
| CpG-ODN 1668 | phosphothioate-modified oligodeoxynucleotides containing a CpG motif:<br>TCC ATG ACG TTC CTG ATG CT,<br>synthesised by NAPS GmbH, Göttingen.<br>Dose: 5 nmol/mouse |

Experimental Groups: 4 Mice Per Group
1. OVA$_{257-264}$
2. pR60
3. CpG 1668+OVA$_{257-264}$
4. CpG 1668+pR60+OVA$_{257-264}$ Mice were injected into each hind footpad with a total volume of 100 μl (50 μl per footpad), containing the above mentioned compounds. One hour after injection blood was taken from the tail-vein and serum was prepared. The amount of the pro-inflammatory cytokines TNF-α and IL-6 in the sera was determined by cytokine-specific ELISAs according to the manufacturer's instructions (R&D Systems, Inc., Minneapolis, Minn.).

Figure 4:
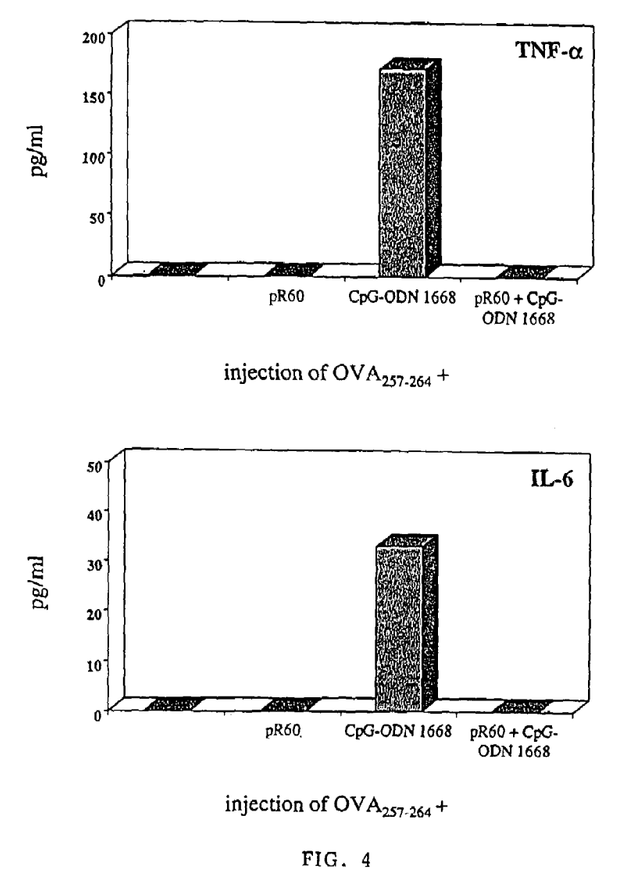
FIG. 4 shows that co-injected poly-L-arginine prevents the CpG-ODN-induced systemic production of TNF-α and IL-6 in vivo. Mice were injected into the hind footpads and one hour later serum was prepared. The amount of TNF-α and IL-6 in the sera was determined by ELISA.

This experiment shows that injection of OVA$_{257-264}$ alone or in combination with poly-L-arginine does not induce the production of detectable amounts of TNF-α or IL-6 (FIG. 4). In contrast, the injection of OVA$_{257-264}$-peptide with CpG-ODN 1668 induces the systemic production of TNF-α and IL-6. When peptide and CpG-ODN were co-injected with poly-L-arginine, the CpG-ODN induced production of pro-inflammatory cytokines was inhibited.

REFERENCES

Andreu, D., and Rivas, L. (1998). Animal antimicrobial peptides: an overview. Biopolymers 47, 415–433.

Ganz, T. (1999). Defensins and host defense [comment]. Science 286, 420–421.

Ganz, T., and Lehrer, R. I. (1999). Antibiotic peptides from higher eukaryotes: biology and applications. Mol Med Today 5, 292–297.

Goldman, R., Bar-Shavit, Z. (1983). On the mechanism of the augmentation of the phagocytic capability of phagocytic cells by Tuftsin, substance P, neurotensin, and kentsin and the interrelationship between their receptors. Ann N Y Aca. Sci. 419:143–55.

Inaba et al. (1992). Generation of large numbers of dendritic cells from mouse bone marrow cultures supplemented with granulocyte/macrophage colony-stimulating factor. J. Exp. Med. 176:1693

Hancock, R. E. (1999). Host defence (cationic) peptides: what is their future clinical potential? Drugs 57, 469–473.

Lipford, G. B., T. Sparwasser, M. Bauer, S. Zimmermann, E. Koch, K. Heeg, H. Wagner. 1997. Immunostimulatory DNA: sequence-dependent production of potentially harmful or useful cytokines. Eur. J. Immunol. 27:3420

Sparwasser, T. T. Miethke, G. Lipford, A. Erdmann. H. Häcker, K. Heeg, H. Wagner. 1997. Macrophages sense pathogens via DNA motifs: induction of tumor necrosis factor-a-mediated shock. Eur J Immunol. 27:1671

Verdijk, R. M., T. Mutis, B. Esendam, J. Kamp, C. J. Melief, A. Brand, E. Goulmy. 1999. Polyriboinosinic polyribocytidylic acid (poly(I:C)) induces stable maturation of functionally active human dendritic cells. J Immunol. 163:57

The invention claimed is:

1. A method of vaccinating comprising administering to a subject at a subcutaneous, intradermal, transdermal, or intramuscular site of administration polyarginine, and an antigenic polypeptide consisting of a T cell epitope of 8 to 11 amino acids in length, and an immunogenic nucleic acid molecule, wherein a depot effect is induced at the site of administration wherein the depot effect is present at the site of administration 19 days after administration.

2. The method of claim 1, wherein the immunogenic nucleic acid molecule is an oligonucleotide containing nonmethylated cytosine-guanine dinucleotides( CpG-ODN) or an inosine containing oligodeoxynucleotide (I-ODN).

3. A method of vaccinating comprising injecting into a subject at a subcutaneous, intradermal, transdermal, or intramuscular site of administration polyarginine, and an antigenic polypeptide consisting of a T cell epitope of 8 to 11 amino acids in length, and an immunogenic nucleic acid molecule, wherein a depot effect is induced at the site of administration wherein the depot effect is present at the site of administration 19 days after administration.

4. The method of claim 3, wherein the immunogenic nucleic acid molecule is an oligonucleotide containing nonmethylated cytosine-guanine dinucleotides (CpG-ODN) or an inosine containing oligodeoxynucleotide (I-ODN).

* * * * *